United States Patent
Grubbs et al.

(10) Patent No.: US 6,426,419 B1
(45) Date of Patent: Jul. 30, 2002

(54) RUTHENIUM METAL ALKYLIDENE COMPLEXES COORDINATED WITH TRIAZOLYLIDENE LIGANDS THAT EXHIBIT HIGH OLEFIN METATHESIS ACTIVITY

(75) Inventors: Robert H. Grubbs, South Pasadena; Tina M. Trinka, Pasadena, both of CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 09/539,840

(22) Filed: Mar. 31, 2000

Related U.S. Application Data
(60) Provisional application No. 60/127,469, filed on Mar. 31, 1999.

(51) Int. Cl.⁷ .............................. C07F 15/00; C07F 9/00; B01J 31/00; C08F 4/80
(52) U.S. Cl. .................. 548/101; 548/262.2; 556/136; 556/22; 502/155; 526/171
(58) Field of Search .............................. 548/101, 262.2; 556/136, 22; 502/155; 526/171

(56) References Cited

U.S. PATENT DOCUMENTS

| | | | |
|---|---|---|---|
| 5,312,940 A | 5/1994 | Grubbs et al. | 556/136 |
| 5,342,909 A | 8/1994 | Grubbs et al. | 526/171 |
| 5,710,298 A | 1/1998 | Grubbs et al. | 556/22 |
| 5,728,839 A | 3/1998 | Herrmann et al. | 548/103 |
| 5,728,917 A | 3/1998 | Grubbs et al. | 585/653 |
| 5,750,815 A | 5/1998 | Grubbs et al. | 585/511 |
| 5,831,108 A | 11/1998 | Grubbs et al. | 556/21 |
| 6,025,496 A | * 2/2000 | Herrmann et al. | 548/107 |

FOREIGN PATENT DOCUMENTS

| | | | |
|---|---|---|---|
| DE | 19629523 A1 | | 1/1998 |
| DE | 198 15 275 A 1 | * | 7/1999 |
| WO | Wo 97/20865 | | 6/1997 |
| WO | WO 97/29135 | | 8/1997 |
| WO | WO 99/51344 | | 10/1999 |

OTHER PUBLICATIONS

Huang, Jinkun, et al., Influence of Sterically Demanding Carbene Ligation on Catalytic Behavior and Thermal Stability of Ruthenium Olefin Metathesis Catalysts, *Organometallics*, 1999, 5375–5380.

Weskamp, Thomas, et al., N–Heterocyclic carbenes: state of the art in transition–metal–complex synthesis, *Journal of Organometallic Chemistry*, 600 (2000) 12–22.

Herrmann, Wolfgang A., et al., Complexes of N–Heterocyclic Carbenes, Anorganisch–chemisches Institut der Technischen Universitat, 85–111 (2000).

Herrmann, Wolfgang A., et al., Nickel(II) Complexes of N–Heterocyclic Carbenes, *Organometallics*, 1997, 2209–2212.

Hermann et al., "A Novel Class of Ruthenium Catalysts for Olefin Metathesis" Abstract: 11$^{th}$ International Symposium on Homogenous Catalysis, University of St. Andrews, Scotland, UK, Jul. 1998.*

Weskamp et al., "A Novel Class of Ruthenium Catalysts for Olefin Metathesis" Angewandte Chemie International, vol.37, No. 18, pp. 2490–2493 (Oct. 2, 1998).*

* cited by examiner

*Primary Examiner*—Porfirio Nazario-Gonzalez
(74) *Attorney, Agent, or Firm*—Pillsbury Winthrop LLP

(57) ABSTRACT

The invention discloses ruthenium alkylidene complexes of the type $(PCy_3)(L)Cl_2Ru(CHPh)$, where L is a triazolylidene ligand of the general formula:

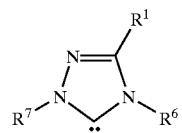

These catalysts have been found to be considerably more active for olefin metathesis at elevated temperatures than the parent catalyst $(PCy_3)_2Cl_2Ru(CHPh)(2)$. For example, complex 14 (L=1,3,4-triphenyl-4.5-dihydro-1H-triazol-5-ylidene) is able to catalyze the ring-closing metathesis of substituted dienes to give tetra-substituted cyclic olefins in good yield. In addition, this complex demonstrates the analogous stability towards oxygen and moisture exhibited by ruthenium alkylidene 2.

35 Claims, 1 Drawing Sheet

RUTHENIUM METAL ALKYLIDENE COMPLEXES COORDINATED WITH TRIAZOLYLIDENE LIGANDS THAT EXHIBIT HIGH OLEFIN METATHESIS ACTIVITY

This application claims the benefit of U.S. Provisional Patent Application Ser. No. 60/127,469, filed Mar. 31, 1999, the contents of which are herein incorporated by reference in its entirety.

The U.S. Government has certain rights in this invention pursuant to Grant No. 9509745 awarded by the National Science Foundation.

BACKGROUND

Metathesis catalysts have been previously described by for example, U.S. Pat. Nos. 5,312,940, 5,342,909, 5,728,917, 5,750,815, 5,710,298, and 5,831,108 and PCT Publications WO 97/20865 and WO 97/29135 which are all incorporated herein by reference. These publications describe well-defined single component ruthenium or osmium catalysts that possess several advantageous properties. For example, these catalysts are tolerant to a variety of functional groups and are more active than previously known metathesis catalysts. Olefin metathesis is a carbon-carbon bond breaking/bond making process in which there is an overall exchange of double bond moieties between two olefins. The. three main ways that olefin metathesis can be applied are illustrated in Scheme 1. Ring-opening metathesis polymerization (ROMP) involves the formation of polyolefins from strained cyclic olefins; ring-closing metathesis (RCM) involves the intramolecular transformation of an alpha, omega-diene to a cyclic olefin; and acyclic diene metathesis (ADMET) involves the intermolecular exchange of olefins.

Scheme 1

Figure 1A:
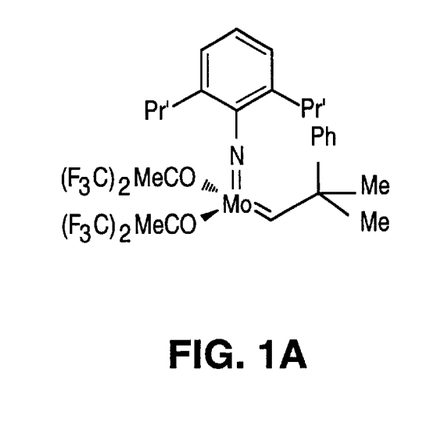
FIG. 1A shows an example of a Schrock molybdenum catalyst.
Figure 1B:
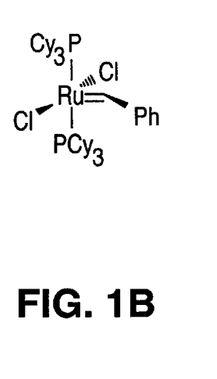
FIG. 1B shows an example of a Grubbs ruthenium alkylidene catalyst.

Olefin metathesis can be mediated by a number of transition metals, but the two most widely used catalysts are the Schrock molybdenum alkylidene (1) and the Grubbs ruthenium alkylidene (2). FIGS. 1A and 1B show examples of these two catalysts.

The commercial availability and high activity of these well-defined, single-component catalysts has led to the development of olefin metathesis as a standard synthetic method. In particular, RCM has been applied to a diverse array of problems, ranging from the total synthesis of natural products to the synthesis of catenanes. As one review author recently commented, ring-closing metathesis "has come of age as a synthetic technique. It is no longer a novelty, to be included in the title of every paper, it is a synthetic tool available to every practicing organic synthetic chemist."

Yet, there is still considerable room for improvement. Neither 1 nor 2 is a "perfect" catalyst; each has significant problems associated with it. Although the Schrock alkylidene (1) has the greater overall activity, it suffers from extreme air and moisture sensitivity, and it lacks tolerance for many functional groups (e.g. alcohols, aldehydes, and carboxylic acids). On the other hand, the Grubbs alkylidene (2) is easier and less expensive to make, is air stable as a solid and has a much wider functional group tolerance, but its activity is limited to at least two orders of magnitude less than 1. Additionally, neither 1 nor 2 provides stereoselective control over the metathesis products.

Figure 2A:
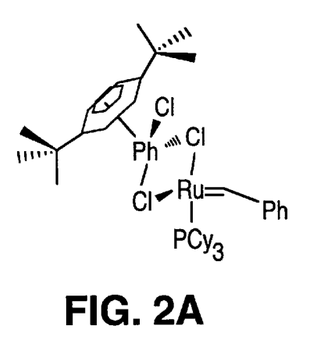
FIGS. 2A, 2B and 2C show examples of ligand modifications of the Grnbbs ruthenium alkylidene catalyst.
Figure 2B:
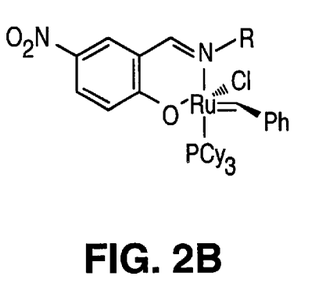
Figure 2C:
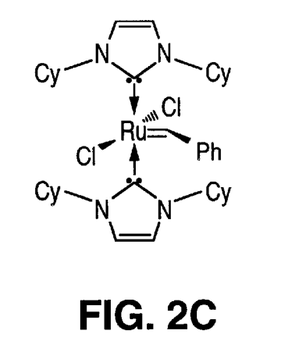

Because of these problems, the design of metathesis catalysts with better activity, stability, and selectivity is an area of active investigation. Recently, several modifications of complex 2 have been reported, including a heterobimetallic complex (3), a bidentate Schiff base supported complex (4), and a bis (N-heterocyclic carbene) substituted complex (5). FIGS. 2A, 2B and 2C show examples of each of these liganids.

Complex 3 is approximately 80 times more active than 2 for the ROMP of 1,5-cyclooctadiene, and so it can be used as an alternative in RCM reactions that would proceed too slowly with 2 to be practical. However, at the same time, 3 is also more unstable than 2 and decomposes more rapidly. Complex 4 is more active at elevated temperatures than 2 for RCM, and it has the advantage of remaining active in polar protic media. Finally, complex 5 displays ROMP and RCM activity at elevated temperatures that is comparable to the activity of 2 at room temperature.

Thus, there is a need for a stable, more active metathesis catalyst. The invention address this need by providing for mono-substituted derivatives as more active metathesis catalysts than those previously examined. In addition, the invention provides a method of attaching N-heterocyclic carbene ligands to a metal center and methods of using the same.

SUMMARY OF THE INVENTION

The present invention relates to novel metathesis catalysts with a tliazolylidene-based ligand and methods for preparing and using the same. Preferred embodiments of the catalysts of the present invention are of the general formula wherein:

X and $X^1$ are each independently an anionic ligand;

L is a neutral electron donor ligand;

R, $R^1$ $R^6$ and $R^7$ are each independently hydrogen or a substituent selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl and $C_1$–$C_{20}$ alkylsulfinyl. Optionally, each of the R, $R^1$, $R^6$ and $R^7$ substituent groups may be independently substituted with one or more moieties selected from the group consisting of $C_1$–$C_{10}$ alkyl, $C_1$–$C_{10}$ alkoxy, and aryl which in turn may each be further substituted with one or more groups selected from a halogen, a $C_1$–$C_5$ alkyl, $C_1$–$C_5$ alkoxy, and phenyl. Moreover, any of the catalyst ligands may further include one or more functional groups. Examples of suitable functional groups include but are not limited to: hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen. The inclusion of a triazolylidene ligand to the previously described ruthenium or osmium catalysts has been found to dramatically improve the properties of these complexes. In particular, the new catalyst has been shown to be remarkably more active at elevated temperatures for metathesis reactions such as the ring-opening metathesis polymerization of cyclic monomers and the ring closing metathesis of dienes.

DETAILED DESCRIPTION OF THE PREFERRED EMBODIMENTS

The present invention generally relates to ruthenium carbene catalysts for use in olefin metathesis reactions. More particularly, the present invention relates to triazolylidene-based ruthenium carbene catalysts and methods for making the same.

Unmodified ruthenium and osmium carbene complexes have been described in U.S. Pat. Nos. 5,312,940, 5,342,909, 5,728,917, 5,750,815, and 5,710,298, all of which are incorporated herein by reference. The ruthenium and osmium carbene complexes disclosed in these patents all possess metal centers that are formally in the +2 oxidation state, have an electron count of 16, and are penta-coordinated. These catalysts are of the general formula wherein:

M is ruthenium or osmium;

X and $X^1$ are each independently any anionic ligand;

L and $L^1$ are each independently any neutral electron donor ligand;

R and $R^1$ are each independently hydrogen or a substituent selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl and $C_1$–$C_{20}$ alkylsulfinyl. Optionally, each of the R or $R^1$ substituent group may be substituted with one or more moieties selected from the group consisting of $C_1$–$C_{10}$ alkyl, $C_1$–$C_{10}$ alkoxy, and aryl which in turn may each be further substituted with one or more groups selected from a halogen, a $C_1$–$C_5$ alkyl, $C_1$–$C_5$ alkoxy, and phenyl. Moreover, any of the catalyst ligands may further include one or more functional groups.

Examples of suitable functional groups include but are not limited to: hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

In preferred embodiments of these catalysts, the R subistituenlt is hydrogen and the $R^1$ substituent is selected from the group consisting of $C_1$–$C_{20}$ alkyl, $C_2$–$C_{20}$ alkenyl, and aryl. In even more preferred embodiments, the $R^1$ substituent is phenyl or vinyl, optionally substituted with one or more moieties selected fiom the group consisting of $C_1$–$C_5$ alkyl, $C_1$–$C_5$ alkoxy, phenyl, and a functional group. In especially preferred embodiments, $R^1$ is phenyl or vinyl substituted with one or more moieties selected from the group consisting of chloride, bromide, iodide, fluoride, —$NO_2$, —$NMe_2$, methyl, methoxy and phenyl. In the most preferred embodiments, the $R^1$ substituent is phenyl or —$C$=$C(CH_3)_2$.

In preferred embodiments of these catalysts, L and $L^1$ are each independently selected from the group consisting of phosphine, sulfonated phosphine, phosphite, phosphinite, phosphonite, arsine, stibine, ether, amine, amide, imine, sulfoxide, carboxyl, nitrosyl, pyridine, and thioether. In more preferred embodiments, L and $L^1$ are each a phosphine of the formula $PR^3R^4R^5$, where $R^3$, $R^4$, and $R^5$ are each independently aryl or $C_1$–$C_{10}$ alkyl, particularly primary alkyl, secondary alkyl or cycloalkyl. In the most preferred embodiments, L and $L^1$ ligands are each selected from the group consisting of -P(cyclohexyl)$_3$, -P(cyclopentyl)$_3$, -P(isopropyl)$_3$, and -P(phenyl)$_3$.

In preferred embodiments of these catalysts, X and $X^1$ are each independently hydrogen, halide, or one of the following groups: $C_1$–$C_{20}$ alkyl, aryl, $C_1$–$C_{20}$ alkoxide, aryloxide, $C_3$–$C_{20}$ alkyldiketonate, aryldiketonate, $C_1$–$C_{20}$ carboxylate, arylsulfonate, $C_1$–$C_{20}$ alkylsulfonate, $C_1$–$C_{20}$ alkylthio, $C_1$–$C_{20}$ alkylsulfonyl, or $C_1$–$C_{20}$ alkylsulfinyl. Optionally, X and $X^1$ may be substituted with one or more moieties selected from the group consisting of $C_1$–$C_{10}$ alkyl, $C_1$–$C_{10}$ alkoxy, and aryl which in turn may each be further substituted with one or more groups selected from halogen, $C_1$–$C_5$ alkyl, $C_1$–$C_5$ alkoxy, and phenyl. In more preferred embodiments, X and $X^1$ are halide, benzoate, $C_1$–$C_5$ carboxylate, $C_1$–$C_5$ alkyl, phenoxy, $C_1$–$C_5$ alkoxy, $C_1$–$C_5$ alkylthio, aryl, and $C_1$–$C_5$ alkyl sulfonate. In even more preferred embodiments, X and $X^1$ are each halide, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, or trifluoromethanesulfonate. In the most preferred embodiments, X and $X^1$ are each chloride.

The catalysts of the present invention are as described above except that $L^1$ is an unsubstituted or substituted triazolylidene of the general formula:

wherein:

$R^6$ and $R^7$ are each independently hydrogen or a substituent selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl and $C_1$–$C_{20}$ alkylsulfinyl. In addition, each of the $R^6$ and $R^7$ substituent groups may be substituted with one or more moieties selected from the group consisting of $C_1$–$C_{10}$ alkyl, $C_1$–$C_{10}$ alkoxy, and aryl which in turn may each be further substituted with one or more groups selected from a halogen, a $C_1$–$C_5$ alkyl, $C_1$–$C_5$ alkoxy, and phenyl. Moreover, each of the $R^6$ and $R^7$ substituent groups may further include one or more functional groups. Examples of suitable functional groups include but are not limited to: hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

Optionally, $R^6$ and $R^7$ together may form a cycloalkyl or an aryl moiety. In preferred embodiments, $R^6$ and $R^7$ are both hydrogen or phenyl, or $R^6$ and $R^7$ together form a cycloalkyl group.

Without being bound by theory, it is believed that bulkier $R^6$ and $R^7$ groups result in catalysts with improved characteristics such as thermal stability. In even more preferred embodiments, $R^6$ and $R^7$ are the same and each is independently of the formula wherein:

$R^8$, $R^9$, and $R^{10}$ are each independently hydrogen, substituted or unsubstituted $C_1$–$C_{10}$ alkyl, $C_1$–$C_{10}$ alkoxy, aryl, or a functional group selected from hydroxyl, thiol, thioether, ketone, aldehyde, ester, ether, amine, imine, amide, nitro, carboxylic acid, disulfide, carbonate, isocyanate, carbodiumide, carboalkoxy, carbamate, and halogen. In the most preferred embodiments, $R^8$, $R^9$, and $R^{10}$ are the same and are each methyl.

As stated above, $R^1$ may be hydrogen or a substituent selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl and $C_1$–$C_{20}$ alkylsulfinyl. Optionally, the $R^1$ substituent group may be substituted with one or more moieties selected from the group consisting of $C_1$–$C_{10}$ alkyl, $C_1$–$C_{10}$ alkoxy, and aryl which in turn may each be further substituted with one or more groups selected from a halogen, a $C_1$–$C_5$ alkyl, $C_1$–$C_5$ alkoxy, and phenyl. Moreover, any of the catalyst ligands may further include one or more functional groups. Examples of suitable functional groups include but are not limited to: hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen. In preferred embodiments, $R^1$ is either substituted or unsubstituted aryl.

A preferred embodiment of the catalyst is of the general formula:

14

Another embodiment of the invention includes both L and $L^1$ being an unsubstituted or substituted triazolylidene. In this embodiment, R, $R^1$, $R^6$, $R^7$, X and $X^1$ are as described above.

Metathesis Reactions

The catalysts of the invention may be used for any metathesis reaction (i.e. ring opening metathesis polymerization, ring closing metathesis, cross metathesis, etc.) by contacting the inventive catalysts with an appropriate olefin. The RCM activity of an exemplary catalyst complex 14 in comparison to the Schrock (1) and Grubbs (2) catalysts is summarized in Table 1. Specifically, Table 1 shows the percent conversion in the RCM of substrates with 1, 2, and 14. This series of substrates was chosen in order to probe the ability of these new complexes to initiate ling-lo sing metathesis (RCM), and also to determine if they have any effect on the stereoselectivity of the RCM reaction. As seen, E=$CO_2$Et where the percent conversion and E:Z ratios were determined by $^1$H NMR Integration. The conditions under which the reactions took place for catalyst 14 are as follows: 5 mol % catalyst, 0.10 in $C_2D_6$, 65° C. The conditions under which the reactions took place for catalyst 1 are as follows: 5 mol % catalyst, 0.05M $CD_2Cl_2$, 40° C.

In the case of di ethyl diallylmalonate, the first substrate, initial screening revealed that the activity of complex 14 is relatively slow at room temperature (25° C.). For example, with a catalyst loading of 5 mol % at a concentration of 0.05M in $CD_2Cl_2$, the Grubbs catalyst (2) takes less than 30 minutes to complete the cyclization, while complex 14 takes 8 hours to accomplish the same conversion. However. the activity of 14 increased dramatically at elevated temperatures. At ~40° C., it is able to cyclize diethyl diallylmalonate within 30 minutes.

TABLE 1

| Substrate | Product | Catalyst 1* | Catalyst 2* | Catalyst 14* |
|---|---|---|---|---|
| ![E,E diene] | ![cyclopentene diester] | — | 30 min 100% | 30 min 100% |
| ![E,E methylated diene] | ![methylcyclopentene diester] | 100% | 30 min 82% | 30 min 98% |

TABLE 1-continued

| Substrate | Product | Catalyst 1* | Catalyst 2* | Catalyst 14* |
|---|---|---|---|---|
| [structure: E,E,Bu$^t$ diene] | [structure: cyclopentene with E,E and Bu$^t$] | 96% | no reaction | 30 min 85% |
| [structure: dimethyl diene with E,E] | [structure: methylcyclopentene with E,E] | 96% | no reaction | 30 min 53% |
| [structure: dimethyl octadiene with E,E] | [structure: dimethylcyclohexene with E,E] | 61% | no reaction | 30 min 82% |
| [structure: triethylene glycol diallyl ether] | [structure: crown ether macrocycle] | — | 60 min 39% E:Z = 1.6:1 | 30 min 73% E:Z = 2.3:1 |

Complex 14 showed superior activity for even more sterically challenging substrates. While complex 2 is not able to ring-close 2-t-butyl diethyl diallylmalonate, 4,4'-dicarbethoxy-2,6-dimethyl-1,6-heptadiene, or 4,4'-dicarbethoxy-2,7-dimethyl-1,7-octadiene, 14 was active for this transformation (Table 1). The conversions at ~40° C. ranged from moderate (53%) to very good (85%) for these substrates. This activity is significant because, up until now, the only metathesis catalyst able to ring-close highly substituted dienes to yield tri- and tetra-substituted olefins has been the Schrock alkylidene (1). In fact, the new catalyst (14) shows improved activity over the Schrock molybdenum alkylidene in the RCM of 4,4'-dicarbethoxy-2,7-dimethyl-1.7-octadiene (82% conversion for 14 vs. 61% for 1).

The RCM of triethylene glycol diallyl ether was tested in order to determine if this new catalyst had any effect on cis,trans-stereoselectivity. Complex 14 produced a product mixture with an E:Z ratio of approximately 2.3:1, which is only somewhat greater than the ratio of 1.6:1 observed for complex 2.[17] Interestingly, when the reaction with catalyst 14 was allowed to proceed at room temperature (44%. conversion after 20 hours), the observed E:Z ratio was 5:1. The relatively high proportion of trans product is due to the reaction reaching equilibrium during the extended reaction time.

In addition to RCM activity, the novel catalyst (e.g., complex 14) is able to catalyze the ROMP of cyclic olefins. Because these new ruthenium-based olefin metathesis catalysts coordinated with N-heterocyclic carbene ligands display such high activity, they are capable of mediating the ROMP of more challenging monomers, such as those that are less-strained and sterically bulky. For example, these new catalysts can ROMP trisubstituted cyclooctene derivatives and cyclooctatetraene derivatives, toward which the parent bis(phosphine) catalyst 2 is inactive. In addition, these new catalysts are capable of polymerizing the more highly strained and sterically less bulky monomers traditionally polymerized by 2, such as cyclopropenes, cyclobutenes, benzocyclobutenes, cyclopentenes, cyclopentadiene oligomers, cyclohexenes, cycloheptenes, cyclooctenes, cycooctadienes, norbornenes, norbornadienes, [2.2.1]bicycloheptenes, [2.2.2]bicyclooctenes, cyclohexenylnorbornenes, and norbornene dicarboxylic anhydrides. Preferably, the novel catalyst is able to catalyze the ROMP of dicyclopentadiene. When just a fractional mol % of catalyst is added to vigorously stirred, warmed (~40° C.) dicyclopentadiene, the polymerization reaction occurs within minutes to yield a solid mass of yellow material. For example, Scheme 2 shows the use of 0.1 mol % of complex 14 to ROMP dicyclopentadiene (DCPD).

Scheme 2

Further, complex 14 was more active in situ for ROMP than the general Grubbs complex 2 with L=PPh₃. For example, the PPh₃ derivative of complex 2 is not active enough to initiate the ROMP of DCPD. However, as shown in Scheme 3, when the PPh₃ derivative of complex 2 was combined with the triazolylidene alkoxide adduct 12 in DCPD and Synthesis

In general, the catalysts of the present invention are prepared by substituting one of the L groups in the previously described ruthenium catalysts (wherein L=L¹), LLXX¹M=CRR¹, with a tliazolylidene ligand. Scheme 4 shows the currently accepted mechanism of olefin metathesis by ruthenium alkylidenes.

Scheme 4 warmed to 60–70° C., a more active catalyst formed in situ that was able to perform the ROMP reaction.

Scheme 3

This type of complex has been shown to be remarkably more active at elevated temperatures for metathesis than the parent complex $(PCy_3)_2Cl_2Ru(CHPh)$ (2). For example, complex 14 (L=1,3,4-triphenyl-4,5-dihydro-1H-triazol-5-ylidene) is able to ring-close highly substituted dienes to give tetra-substituted cyclic olefins in good yields. To date, this reaction has not been possible with complex 2. In addition to enhanced activity, complex 14 demonstrates the analogous stability towards oxygen and moisture that is exhibited by complex 2. Complex 14 is also able to initiate the ring-opening metathesis polymerization of dicyclopentadiene. Thus, it has been possible to combine the many desirable properties of the ruthenium alkylidene (2) with the higher activity of the Schrock molybdenum alkylidene (1) in a new catalyst.

The proposed mechanism in Scheme 4 has been determined through extensive kinetic and reactivity studies, and it corroborates well with recently determined thermochemical data. As shown, the main steps in the reaction involve: 1) olefin coordination cis to the alkylidene, ii) alkylidene rotation and dissociation of a phosphine, iii) formation of a metallacyclobutane intermediate, and finally, iv) formal retrocycloaddition to complete the metathesis reaction.

The most important aspect about the above mechanism that is pertinent to this discussion is that the most active species is a mono (phosphine) intermediate, which requires Ru—P bond cleavage. Consistent with this mechanism, it has been found that both more sterically bulky and more electron donating phosphines increase the catalyst activity, since these properties facilitate phosphine dissociation and/or stabilization of the mono (phosphine) intermediate. In addition, it has been proposed that more electron donating phosphines also favor the formation of the metallocyclobutane intermediate. Using this concept, the ruthenium alkylidene complex with an N-heterocyclic ligand of the invention would be a more active metathesis catalyst because of the ligand's strong electron donating character. Furthermore, it is proposed that the more liabile phospine would dissociate, giving a mono (N-heterocyclic carbene) intermediate as the active species.

As ligands, the N-heterocyclic carbenes are characterized as pure sigma-donors. As a result, the N-heterocyclic carbenes are able to form complexes with all metals, from transition elements in both high and low oxidation states to the main group metals and the lanthanides. Several studies have focused on the applications and advantages of these ligands in comparison to conventional donor ligands, such as tertiary phosphines. In a number of cases, the metal-carbene bond has been found to be remarkably robust. For example, the palladium complex $L_2PdI_2$ where L=1,3-dimethyl-2,3-dihydro-1H-imidazol-2-ylidene, remained intact within the presence of oxygen in boiling THF for several days.

Thus, the N-heterocyclic carbene ligands incorporate several characteristics that would be advantageous in making an improved olefin metathesis catalyst. Most importantly, these ligands are stronger electron donors than phosphines, which according to the accepted mechanism of olefin metathesis, should make a mono-substituted analog of the type shown in FIG. 3 even more active than the parent complex (2). Previous work has also indicated that metal-carbene bonds of this kind are thermally stable and resistant to dissociation. Finally, the synthesis of N-heterocyclic carbene derivatives is relatively straightforward, so it would be possible to rapidly investigate the effects of steric and electronic changes to the ligand on catalyst activity.

Thus, considering the electron donating characteristics of these ligands, the invention provides a method for attaching a N-heterocyclic carbene ligand to the metal center of a ruthenium metathesis catalyst. The preferred N-heterocyclic carbene ligand is triazolylidene. In the first step, a salt is prepared from an N-mono(substituted) amide as follows:

Alternatively, the product may be made directly from the salt by generating the carbene in situ as shown in Scheme 7.

Scheme 5

Next, and as shown in Scheme 6, the salt may be converted to a substituted or unsubstituted primary alkyl oxide, for example, a $C_1$–$C_3$ alkyl oxide. Moreover, the primary alkyl oxide may include one or more functional groups. Examples of suitable functional groups include but are not limited to: hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen. Preferably, the salt is converted to a methoxide. In the preferred embodiment, the methoxide is then reacted with reacted with $LLXX^1M=CRR^1$ (previously described ruthenium metathesis catalyst) to yield a triazolylidene based ruthenium carbene catalyst.

Scheme 6

Scheme 7

Finally, the free carbene can be reacted with $LLXX^1M=CRR^1$ (previously described ruthenium metathesis catalyst) to yield a triazolylidene based ruthenium carbene catalyst as shown in Scheme 8.

Scheme 8

Examples of other N-heterocyclic carbenes that may be used with the invention are:

For the purposes of clarity, the specific details of the invention will be illustrated with reference to especially preferred embodiments. However, it should be appreciated that these embodiments and examples are for the purposes of illustration only and are not intended to limit the scope of the invention.

REPRESENTATIVE EXPERIMENTAL PROTOCOLS

Synthesis of $(PCy_3)(L)Cl_2Ru(CHPh)[L=1,3,4$-triphenyl-4,5-dihydro-1H-triazol-5-ylidene]. The target was chosen to be a mono-substituted complex containing a triazolylidene ligand (14). The synthesis of the 1,3,4-triphenyl substituted tuiazolylidene (13) has been previously reported. As shown in Scheme 9, the route to the triazolium salt involves the preparation of N-phenylbenzimidoyl chloride (9) from benzanilide (8), followed by reaction with phenylhydrazine to give a mixture of N-phenylbenzamide phenylhydrazone (10) and N-amino-N,N-diphenyl benzamide. The N-phenylbenzamide phenylhydrazone is then converted to the triazolium salt by cyclocondensation with formic acid. The perchlorate salt (11) is obtained by treatment with perchloric acid. Finally, the triazoliuni salt can then be readily converted to the methoxide (12), as shown in Scheme 10, which eliminates methanol upon heating under reduced pressure to give the free carbene (13).

Scheme 9

One equivalent of the isolated carbene reacted with (PCy$_3$)(L)Cl$_2$Ru(CHPh) (2) in toluene at room temperature to give the mono-substituted complex 14 (Scheme 10). The ligand exchange occurred remarkably quickly (within 5 minutes). Alternatively, it was found that the product could be made directly from the reaction of the methoxide (12) and 2 in toluene at 80° C. for 5–10 minutes. This route was used to prepare complex 14 on a 0.6 g scale in 59% yield. The free PCy$_3$ byproduct could be readily separated by crystallization of the product from pentane at −78° C. Furthermore, the product could also be made directly from the triazolium salt (11) by generating the carbene in situ as shown in Scheme 10.

The product of these reactions (14) is actually a mixture of two species. By $^1$H NMR, two resonances for alkylidene alpha-protons were observed, one at 20.04 ppm (doublet, $^3J_{HP}$=9.6 Hz % 1,=9.6 Hz) and the other at 19.84 ppm (doublet, $^3J_{HP}$=7.5 Hz). These two resonances appeared consistently in a 1.5 to 1 ratio. The fact that the two alkylidene moieties exhibit different coupling constants is consistent with the products being conformational isomers, in which only the orientations of the triazolylidene ligand and the alkylidene moiety are different. Likewise, the $^{31}$P NMR. showed two resonances, one at 24.14 and the other at 23.04 ppm (both singlets). The composition of the products was further supported by high resolution mass spectrometry data, which showed only one product molecular ion peak. Attempts have not yet been made to separate the isomers. Like complex 2, this product is also air stable as a solid.

General Considerations. All manipulations were carried out using standard Schlenk and vacuum line techniques or in a nitrogen filled drybox. Diethyl diallylmalonate was obtained from Aldrich and degassed before use. Additional RCM substrates were obtained from other group members. Dicyclopentadiene (98%) was obtained from Aldrich and used as received. (PCy$_3$)$_2$Cl$_2$Ru(CHPh) (2) was obtained from a group supply. 1,3,4-Triphenyl-4,5-dihydro-1H-triazol-5-ylidene (13) and its intermediates were prepared as previously reported.[15] NMR solvents were used as received from Cambridge Isotopes. NMR experiments were performed in J. Young gas NMR tubes. $^1$H NMR spectra were recorded on a General Electric QE-300 spectrometer (300.1 MHz for $^1$H). $^{31}$P spectra were recorded on a JEOL JNM-GX400 spectrometer (161.9 MHz $^{31}$P). Chemical shifts are

Scheme 10 reported in parts per million (ppm) downfield from tetramethylsilane with reference to internal solvent for proton spectra. Phosphoric acid was employed as the internal solvent for phosphorus spectra. Mass spectral analysis was performed at the Southern California Mass Spectrometry Facility (University of California at Riverside).

Synthesis of $(PCy_3)(L)Cl_2Ru(CHPh)[L=1,3,4$-Triphenyl-4,5-dihydro-1H-triazol-5-ylidene] (14). In the glovebox, a Schlenk was charged with 0.500 g (0.608 mmol) of $(PCy_3)_2Cl_2Ru(CHPh)$ (2) and 0.195 g (0.592 mmol) of triazolylidene methoxide (12), and then 17 mL toluene were added. The reaction was stirred at room temperature for 20 minutes and at 80° C. for 20 minutes. The brown solution was pumped down under vacuum. Then 100 mL dry pentane was added, and the mixture was gently wanned to dissolve as much material as possible. Upon cooling this solution to −78° C., a tan colored precipitate formed. The supernatant was filtered off via cannula and the product dried under vacuum. Yield=0.293 g (59%). $^1$H NMR ($C_6D_6$) 20.04 (d, $^3J_{HF}$=9.6 Hz), 19.84 (d, $^3J_{HF}$=7.5 Hz); $^{31}$P NMR ($C_6D_6$) 24.14, 23.04; HRMS (FAB) $C_{45}H_{54}Cl_2N_3PRu$ [M] 839.2476, found 839.2450.

Typical RCM experiment. In the glovebox, 5 mol % of complex 14 dissolved in $CD_2Cl_2$ was added to the appropriate amount of a 0.05M solution of substrate in $CD_2Cl_2$. This solution was mixed and 0.75 mL of it was transferred to an NMR tube, which was then sealed. The reaction was either heated at ~40° C. for 30 minutes or left at room temperature, and it was monitored periodically by $^1$H NMR.

Typical ROMP experiment. Approximately 2–3 mgs of complex 14 dissolved in a minimal amount of toluene (0.1–0.2 mL) was added to a small beaker containing 25 mL of vigorously stirred, warmed (40–50° C.) dicyclopentadiene. Reaction occurted within minutes to yield a solid block of yellow polymer.

What is claimed is:

1. A compound of the formula wherein:
X and $X^1$ are either the same or different and are any anionic ligand;
R and $R^1$ are either the same or different and are each independently hydrogen or a substituent selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl and $C_1$–$C_{20}$ alkylsulfinyl, wherein each of the substituents is substituted or unsubstituted;
L is any neutral electron donor; and
wherein $R^6$ and $R^7$ are each independently hydrogen or a moiety selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl and $C_1$–$C_{20}$ alkylsulfinyl, and wherein $R^6$ and $R^7$ are each independently substituted or unsubstituted.

2. The compound of claim 1 wherein the substituent group is substituted with one or more substituted or unsubstituted groups selected from the group consisting of $C_1$–$C_{10}$ alkyl, $C_1$–$C_{10}$ alkoxy, and aryl.

3. The compound of claim 2 wherein the substitutent substitution is substituted with one or more groups selected from the group consisting of halogen, $C_1$–$C_5$ alkyl, $C_1$–$C_5$ alkoxy.

4. The compound of claim 1 wherein the substituent is functionalized with a moiety selected from the group consisting of hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

5. The compound of claim 1 wherein R is hydrogen and $R^1$ is selected from the group consisting of $C_1$–$C_{20}$ alkyl, $C_2$–$C_{20}$ alkenyl, aryl, unsubstituted phenyl, substituted phenyl, unsubstituted vinyl, and substituted vinyl; and wherein the substituted phenyl and substituted vinyl are each independently substituted with one or more groups selected from the group consisting of $C_1$–$C_5$ alkyl, $C_1$–$C_5$ alkoxy, phenyl, hydroxyl, thiol, ketone, aldehyde, ester, ether, amine, imine, amide, nitro, carboxylic acid, disulfide, carbonate, isocyanate, carbodiimide, carboalkoxy, and halogen.

6. The compound of claim 1 wherein L is selected from the group consisting of phosphine, sulfonated phosphine, phosphite, phosphinite, phosphonite, arsine, stibine, ether, amine, amide, imine, sulfoxide, carboxyl, nitrosyl, pyridine, and thioether.

7. The compound of claim 6 wherein L is a phosphine of the formula $PR^3R^4R^5$ wherein $R^3$, $R^4$, and $R^5$ are each independently selected fiom the group consisting of aryl and $C_1$–$C_{10}$ alkyl.

8. The compound of claim 7 wherein $R^3$, $R^4$, and $R^5$ are each independently selected from the group consisting of primary alkyl, secondary alkyl, and cycloalkyl.

9. The compound of claim 7 wherein L is selected from the group consisting of $P(cyclohexyl)_3$, $P(cyclopentyl)_3$, $P(isopropyl)_3$, and $P(phenyl)_3$.

10. The compound of claim 1 wherein X and $X^1$ are each independently selected from the group consisting of hydrogen, halogen, substituted moiety and unsubstituted moiety, wherein the moiety is selected fiom the group consisting of $C_1$–$C_{20}$ alkyl, aryl, $C_1$–$C_{20}$ alkoxide, aryloxide, $C_3$–$C_{20}$ alkyldiketonate, aryldiketonate, $C_1$–$C_{20}$ carboxylate, arylsulfonate, $C_1$–$C_{20}$ alkylsulfonate, $C_1$–$C_{20}$ alkylthio, $C_1$–$C_{20}$ alkylsulfonyl, and $C_1$–$C_{20}$ alkylsulfinyl, and wherein the moiety substitution is selected from the group consisting of $C_1$–$C_{10}$ alkyl, $C_1$–$C_{10}$ alkoxy, and aryl.

11. The compound of claim 1 wherein X and $X^1$ are each independently selected from the group consisting of halide, benzoate, $C_1$–$C_5$ carboxylate, $C_1$–$C_5$ alkyl, phenoxy, $C_1$–$C_5$ alkoxy, $C_1$–$C_5$ alkylthio, aryl, and $C_1$–$C_5$ alkyl sulfonate.

12. The compound of claim 1 wherein X and $X^1$ are each independently selected from the group consisting of halide, $CF_3CO_2$, $CH_3CO_2$, $CFH_2CO_2$, $(CH_3)_3CO$, $(CF_3)_2(CH_3)CO$, $(CF_3)(CH_3)_2CO$, PhO, MeO, EtO, tosylate, mesylate, and trifluoromethanesulfonate.

13. The compound of claim 1 wherein $R^6$ and $R^7$ together form a cycloalkyl or an aryl moiety.

14. The compound of claim 1 wherein $R^6$ and $R^7$ are both hydrogen or phenyl.

15. The compound of claim 1 wherein $R^6$ and $R^7$ are the same and each is independently of the formula wherein:
$R^8$, $R^9$, and $R^{10}$ are each independently hydrogen, $C_1$–$C_{10}$ alkyl, $C_1$–$C_{10}$ alkoxy, aryl, or a functional group selected from hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

16. The compound of claim 15 wherein $R^8$, $R^9$, and $R^{10}$ are the same and are each methyl.

17. A method for synthesizing a compound of the formula comprising:
contacting a compound of the formula:

with a compound of the formula wherein:
M is ruthenium;
X and $X^1$ are either the same or different and are any anionic ligand;
R and $R^1$ are either the same or different and are each independently hydrogen or a substituent selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl and $C_1$–$C_{20}$ alkylsulfinyl, wherein each of the substituents is substituted or unsubstituted;
L and $L^1$ are either the same or difference and are any neutral electron donor;
$R^6$ and $R^7$ are each independently hydrogen or a moiety selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl and $C_1$–$C_{20}$ alkylsulfinyl, wherein $R^6$ and $R^7$ are each independently substituted or unsubstituted; and
W is selected from the group consisting of $C_1$–$C_3$ primary alkyl oxides and wherein W is substituted or unsubstituted.

18. The method of claim 17 wherein the N-heterocyclic carbene ligand is triazolylidene.

19. The method of claim 17 wherein $R^6$ and $R^7$ together form a cycloalkyl or an aryl moiety.

20. The method of claim 17 wherein $R^6$ and $R^7$ are both hydrogen or phenyl.

21. The method of claim 17 wherein $R^6$ and $R^7$ are the same and each is independently of the formula wherein:
$R^8$, $R^9$, and $R^{10}$ are each independently hydrogen, $C_1$–$C_{10}$ alkyl, $C_1$–$C_{10}$ alkoxy, aryl, or a functional group selected from hydroxyl, thiol, thioether, ketone, aldehyde, ester, ether, amine, imine, amide, nitro, carboxylic acid, disulfide, carbonate, isocyanate, carbodiimide, carboalkoxy, carbamate, and halogen.

22. The method of claim 21 wherein $R^8$, $R^9$, and $R^{10}$ are the same and are each methyl.

23. The method of claim 17 wherein W is functionalized with a functional group selected from the group consisting of hydroxyl, thiol, thioether, ketone, aldehyde, ester, ether, amine, imine, amide, nitro, carboxylic acid, disulfide, carbonate, isocyanate, carbodimide, carboalkoxy, carbamate, and halogen.

24. The method of claim 17 wherein W is methoxide.

25. The method of claim 17 wherein X and $X^1$ are each independently selected from the group consisting of hydrogen, halogen, substituted moiety and unsubstituted moiety, wherein the moiety is selected from the group consisting of $C_1$–$C_{20}$ alkyl, aryl, $C_1$–$C_{20}$ alkoxide, aryloxide, $C_3$–$C_{20}$ alkyldiketonate, aryldiketonate, $C_1$–$C_{20}$ carboxylate, arylsulfonate, $C_1$–$C_{20}$ alkylsulfonate, $C_1$–$C_{20}$ alkylthio, $C_1$–$C_{20}$ alkylsulfonyl, and $C_1$–$C_{20}$ alkylsulfinyl, and wherein the moiety substitution is selected from the group consisting of $C_1$–$C_{10}$ alkyl, $C_1$–$C_{10}$ alkoxy, and aryl; and
L and $L^1$ are each independently selected from the group consisting of phosphine, sulfonated phosphine, phosphite, phosphinite, phosphonite, arsine, stibine, ether, amine, amide, imine, sulfoxide, carboxyl, nitrosyl, pyridine, and thioether; and R is hydrogen and $R^1$ is phenyl.

26. The method of claim 25 wherein X and $X^1$ are each chloride and L and $L^1$ are each independently selected from the group consisting of P(cyclohexyl)$_3$, P(cyclopentyl)$_3$, P(isopropyl)$_3$, and P(phenyl)$_3$.

27. The method of claim 17 wherein R is hydrogen, $R^1$, $R^6$ and $R^7$ are each phenyl, L is PPh$_3$, and X and $X^1$ are each chloride.

28. A method for synthesizing a compound of the formula comprising:

contacting a compound of the formula:

with a compound of the formula

29. A method for attaching a N-heterocyclic carbene ligand to a ruthenium metal carbene metathesis complex comprising:

contacting the N-heterocyclic carbene ligand with a compound of the formula wherein

X and $X^1$ are either the same or different and are any anionic ligand;

R and $R^1$ are either the same or different and are each independently hydrogen or a substituent selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkyhthio, $C_1$–$C_{20}$ alkylsulfonyl and $C_1$–$C_{20}$ alkylsulfinyl, wherein each of the substituents is substituted or unsubstituted;

L and $L^1$ are either the same or difference and are any neutral electron donor; and the N-heterocyclic carbene ligand is a triazolylidene ligand of the formula:

wherein $R^6$ and $R^7$ are each independently hydrogen or a moiety selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl and $C_1$–$C_{20}$ alkylsulfinyl, and wherein $R^6$ and $R^7$ are each independently substituted or unsubstituted.

30. The method of claim 29 wherein X and $X^1$ are each independently selected from the group consisting of hydrogen, halogen, substituted moiety and unsubstituted moiety, wherein the moiety is selected from the group consisting of $C_1$–$C_{20}$ alkyl, aryl, $C_1$–$C_{20}$ alkoxide, aryloxide, $C_3$–$C_{20}$ alkyldiketonate, aryldiketonate, $C_1$–$C_{20}$ carboxylate, arylsulfonate, $C_1$–$C_{20}$ alkylsulfonate, $C_1$–$C_{20}$ alkylthio, $C_1$–$C_{20}$ alkylsulfonyl, and $C_1$–$C_{20}$ alkylsulfinyl, and wherein the moiety substitution is selected from the group consisting of $C_1$–$C_{10}$ alkyl, $C_1$–$C_{10}$ alkoxy, and aryl;

L and $L^1$ are each independently selected from the group consisting of phosphine, sulfonated phosphine, phosphite, phosphinite, phosphonite, arsine, stibine, ether, amine, amide, imine, sulfoxide, carboxyl, nitrosyl, pyridine, and thioether; and R is hydrogen and $R^1$ is phenyl.

31. The method of claim 30 wherein X and $X^1$ are each chloride and L and $L^1$ are each independently selected from the group consisting of P(cyclohexyl)$_3$, P(cyclopentyl)$_3$, P(isopropyl)$_3$, and P(phenyl)$_3$.

32. The method of claim 29 wherein the N-heterocyclic carbene ligand is unsaturated.

33. A compound formed by attaching a N-heterocyclic carbene ligand to a ruthenium metal carbene metathesis complex comprising:

contacting the N-heterocyclic carbene ligand with a compound of the formula wherein

X and $X^1$ are either the same or different and are any anionic ligand;

R and $R^1$ are either the same or different and are each independently hydrogen or a substituent selected from the group consisting of $C_1$–$C_{20}$ alkyl, $C_2$–$C_{20}$ alkenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl and $C_1$–$C_{20}$ alkylsulfinyl, wherein each of the substituents is substituted or unsubstituted;

L and $L^1$ are either the same or difference and are any neutral electron donor; and the N-heterocyclic carbene ligand is a triazolylidene ligand of the formula:

wherein $R^6$ and $R^7$ are each independently hydrogen or a moiety selected from the group consisting of $C_1$–$C_{20}$ alkyl, $C_2$–$C_{20}$ alyenyl, $C_2$–$C_{20}$ alkynyl, aryl, $C_1$–$C_{20}$ carboxylate, $C_1$–$C_{20}$ alkoxy, $C_2$–$C_{20}$ alkenyloxy, $C_2$–$C_{20}$ alkynyloxy, aryloxy, $C_2$–$C_{20}$ alkoxycarbonyl, $C_1$–$C_{20}$ alkylthio, $C_1$–$C_{20}$ alkylsulfonyl and $C_1$–$C_{20}$ alkylsulfinyl, and wherein $R^6$ and $R^7$ are each independently substituted or unsubstituted.

34. The compound of claim 33 wherein X and $X^1$ are each independently selected from the group consisting of hydrogen, halogen, substituted moiety and unsubstituted moiety, wherein the moiety is selected from the group consisting of $C_1$–$C_{20}$ alkyl, aryl, $C_1$–$C_{20}$ alkoxide, aryloxide, $C_3$–$C_{20}$ alkyldiketonate, aryldiketonate, $C_1$–$C_{20}$ carboxylate, arylsulfonate, $C_1$–$C_{20}$ alkylsulfonate, $C_1$–$C_{20}$ alkylthio, $C_1$–$C_{20}$ alkylsulfonyl, and $C_1$–$C_{20}$ alkylsulfinyl, and wherein the moiety substitution is selected from the group consisting of $C_1$–$C_{10}$ alkyl, $C_1$–$C_{10}$ alkoxy, and aryl;

L and $L^1$ are each independently selected from the group consisting of phosphine, sulfonated phosphine, phosphite, phosphinite, phosphonite, arsine, stibine, ether, amine, amide, imine, sulfoxide, carboxyl, nitrosyl, pyridine, and thioether; and R is hydrogen and $R^1$ is phenyl.

35. The compound of claim 34 wherein X and $X^1$ are each chloride and L and $L^1$ are each independently selected from the group consisting of P(cyclohexyl)$_3$, P(cyclopentyl)$_3$, P(isopropyl)$_3$, and P(phenyl)$_3$.

* * * * *

Adverse Decision in Interference

Patent No. 6,426,419, Robert H. Grubbs, Tina M. Trnka, NOVEL RUTHENIUM METAL ALKYLIDENE COMPLEXES COORDINATED WITH TRIAZOLYLIDENE LIGANDS THAT EXHIBIT HIGH OLEFIN METATHESIS ACTIVITY, Interference No. 105,364, final judgment adverse to the patentees rendered September 26, 2006, as to claims 1-35.

(*Official Gazette* June 12, 2007)